(12) United States Patent
Gunneson et al.

(10) Patent No.: US 11,246,506 B2
(45) Date of Patent: Feb. 15, 2022

(54) AUTOMATIC SAMPLING ACCESSORY SYSTEM AND METHOD OF DETECTION

(71) Applicant: KONINKLIJKE PHILIPS N.V., Eindhoven (NL)

(72) Inventors: Paul Bruce Gunneson, Cheshire, CT (US); John Russell Delfavero, East Hampton, CT (US)

(73) Assignee: Koninklijke Philips N.V., Eindhoven (NL)

( * ) Notice: Subject to any disclaimer, the term of this patent is extended or adjusted under 35 U.S.C. 154(b) by 501 days.

(21) Appl. No.: 15/751,306

(22) PCT Filed: Aug. 11, 2016

(86) PCT No.: PCT/EP2016/069183
§ 371 (c)(1),
(2) Date: Feb. 8, 2018

(87) PCT Pub. No.: WO2017/025615
PCT Pub. Date: Feb. 16, 2017

(65) Prior Publication Data
US 2018/0235512 A1    Aug. 23, 2018

Related U.S. Application Data

(60) Provisional application No. 62/203,413, filed on Aug. 11, 2015.

(51) Int. Cl.
*A61B 5/097* (2006.01)
*A61B 5/083* (2006.01)
(Continued)

(52) U.S. Cl.
CPC ............ *A61B 5/097* (2013.01); *A61B 5/0836* (2013.01); *A61B 5/087* (2013.01); *A61M 2230/432* (2013.01); *G01N 33/497* (2013.01)

(58) Field of Classification Search
CPC ....... A61B 5/0836; A61B 5/087; A61B 5/097; A61M 2230/432
See application file for complete search history.

(56) References Cited

U.S. PATENT DOCUMENTS

| 4,537,190 A | * | 8/1985 | Caillot | ................. | G01N 33/497 |
| | | | | | 128/204.22 |
| 4,958,075 A | | 9/1990 | Mace et al. | | |

(Continued)

FOREIGN PATENT DOCUMENTS

WO        03105720 A2    12/2003

*Primary Examiner* — Puya Agahi
(74) *Attorney, Agent, or Firm* — Daniel H. Brean

(57) ABSTRACT

A respiratory gas analyzer device (10), such as a capnograph device, is disclosed. A gas measurement component (28), such as a carbon dioxide measurement component in the case of a capnograph, is configured to measure at least one respired gas component (e.g. carbon dioxide). A pump (20) is connected to draw respired gas through the gas measurement component. A pressure gauge (30) is connected to measure pressure in an airflow pathway including the gas measurement component and the pump. An electronic pump controller (40) is programmed to start the pump in response to pressure measured by the pressure gauge satisfying a pump turn on criterion.

10 Claims, 2 Drawing Sheets

(51) Int. Cl.
*A61B 5/087* (2006.01)
*G01N 33/497* (2006.01)

(56) References Cited

U.S. PATENT DOCUMENTS

| | | | |
|---|---|---|---|
| 5,386,833 A | 2/1995 | Uhen | |
| 2007/0221224 A1* | 9/2007 | Pittman | A61M 16/209 |
| | | | 128/204.22 |
| 2009/0241954 A1 | 10/2009 | Karlsson | |
| 2010/0298734 A1 | 11/2010 | Colman et al. | |
| 2012/0302910 A1* | 11/2012 | Freeman | A61M 16/0084 |
| | | | 600/538 |
| 2013/0006134 A1* | 1/2013 | Doyle | A61M 16/0833 |
| | | | 600/532 |
| 2013/0261488 A1 | 10/2013 | Brewer et al. | |
| 2014/0034054 A1* | 2/2014 | Angelico | A61M 16/0003 |
| | | | 128/204.23 |
| 2015/0328417 A1* | 11/2015 | Loser | A61M 16/024 |
| | | | 128/204.23 |
| 2016/0206839 A1 | 7/2016 | Cloutier et al. | |

* cited by examiner

AUTOMATIC SAMPLING ACCESSORY SYSTEM AND METHOD OF DETECTION

This application is a national stage application under 35 U.S.C. § 371 of International Application No. PCT/EP2016/069183 filed on Aug. 11, 2016 and published in the English language on Feb. 16, 2017 as International Publication No. WO2017/025615, which claims priority to U.S. Patent Application No. 62/203,413 filed on Aug. 11, 2015, the entire disclosures of which are incorporated herein by reference.

FIELD

The following relates generally to the respiratory gas analyzer arts, capnography arts, patient accessories for same, and the like.

BACKGROUND

A capnography device monitors the concentration or partial pressure of carbon dioxide ($CO_2$) in respiratory gases. A common capnography parameter is the end-tidal $CO_2$ partial pressure ($PetCO_2$) which conceptually is the $CO_2$ partial pressure at the end of the exhalation phase. However, since this is usually the largest observed $CO_2$ partial pressure in the breathing cycle, $PetCO_2$ is clinically defined as the maximum observed $CO_2$ partial pressure over the breathing cycle. In addition to metrics such as $PetCO_2$, the capnogram waveform provides detailed information when interpreted by a skilled pulmonologist, anesthesiologist, respiratory therapist, or other medical professional.

More generally, a respiratory gas analyzer (or breath gas analyzer) is a device which measures one or more components of respired gases. By way of non-limiting illustration, some other respiratory gas components of clinical interest include oxygen and various volatile organic compounds.

Respiratory gas analyzers may be configured to sample gas in either a main-stream configuration or a side-stream configuration. In the latter configuration, a pump is employed to draw respiratory gas into the $CO_2$ measurement cell. The $CO_2$ measurement is typically based on infrared light absorption by $CO_2$, so that the $CO_2$ measurement cell includes an infrared light source/optical detector assembly.

The capnograph device connects with the patient via a suitable patient accessory (or sampling accessory), which depends upon the type of patient, whether the patient is receiving mechanical ventilation, and other factors. For a patient breathing on their own, or with limited ventilator assistance, the patient accessory may be a nasal cannula, an airway adapter that taps off the main airway path. A pump provides airflow drawing respired air into the $CO_2$ measurement cell.

In such a respiratory gas analyzer employing a pump to sample respired air, the pump is a costly component of the overall analyzer system, and additionally as a mechanical component is prone to failure due to excessive wear. In particular, operating the pump against an "open" airflow circuit produces unnecessary stress on the pump. This can occur if there is no patient accessory connected with the air inlet, or if the patient accessory is connected but not properly coupled to a patient. In addition to adding wear to the pump, operating against an open airflow circuit can draw contamination (dust, airborne particulates, or so forth) into the carbon dioxide measurement cell or other critical components.

One way to address these problems is to employ a mechanical or optical connection switch that activates when a patient accessory is connected to the capnograph device inlet. This approach ensures the pump does not pull on an open airflow circuit due to a missing patient accessory, but does not address the problem of the accessory not being connected with the patient. Additionally, the mechanical or optical switch adds complexity to the capnograph inlet assembly and/or to the patient accessory.

The following discloses a new and improved systems and methods that address the above referenced issues, and others.

SUMMARY

In one disclosed aspect, a respiratory gas analyzer device is disclosed. A gas measurement component is configured to measure at least one respired gas component. A pump is connected to draw respired gas through the gas measurement component. A pressure gauge is connected to measure pressure in an airflow pathway including the gas measurement component and the pump. An electronic pump controller is programmed to start the pump in response to pressure measured by the pressure gauge satisfying a pump turn on criterion.

In another disclosed aspect, a capnograph device is disclosed. A carbon dioxide measurement component is configured to measure carbon dioxide in respired gas. A pump is connected to draw respired gas through the carbon dioxide measurement component. A pressure gauge is connected to measure pressure of the respired gas drawn through the carbon dioxide measurement component by the pump. An electronic pump controller is programmed to start the pump in response to pressure measured by the pressure gauge satisfying a pump turn on criterion.

One advantage resides in providing reduced pump wear in a capnograph or other respiratory gas analyzer device.

Another advantage resides in providing pump turn-on in a capnograph or other respiratory gas analyzer device operating in a sidestream mode, in which the pump is turned on in response to positive metrics indicating a patient is actually operatively connected.

Another advantage resides in a capnograph or other respiratory gas analyzer device operating in sidestream mode with reduced manufacturing and maintenance cost.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
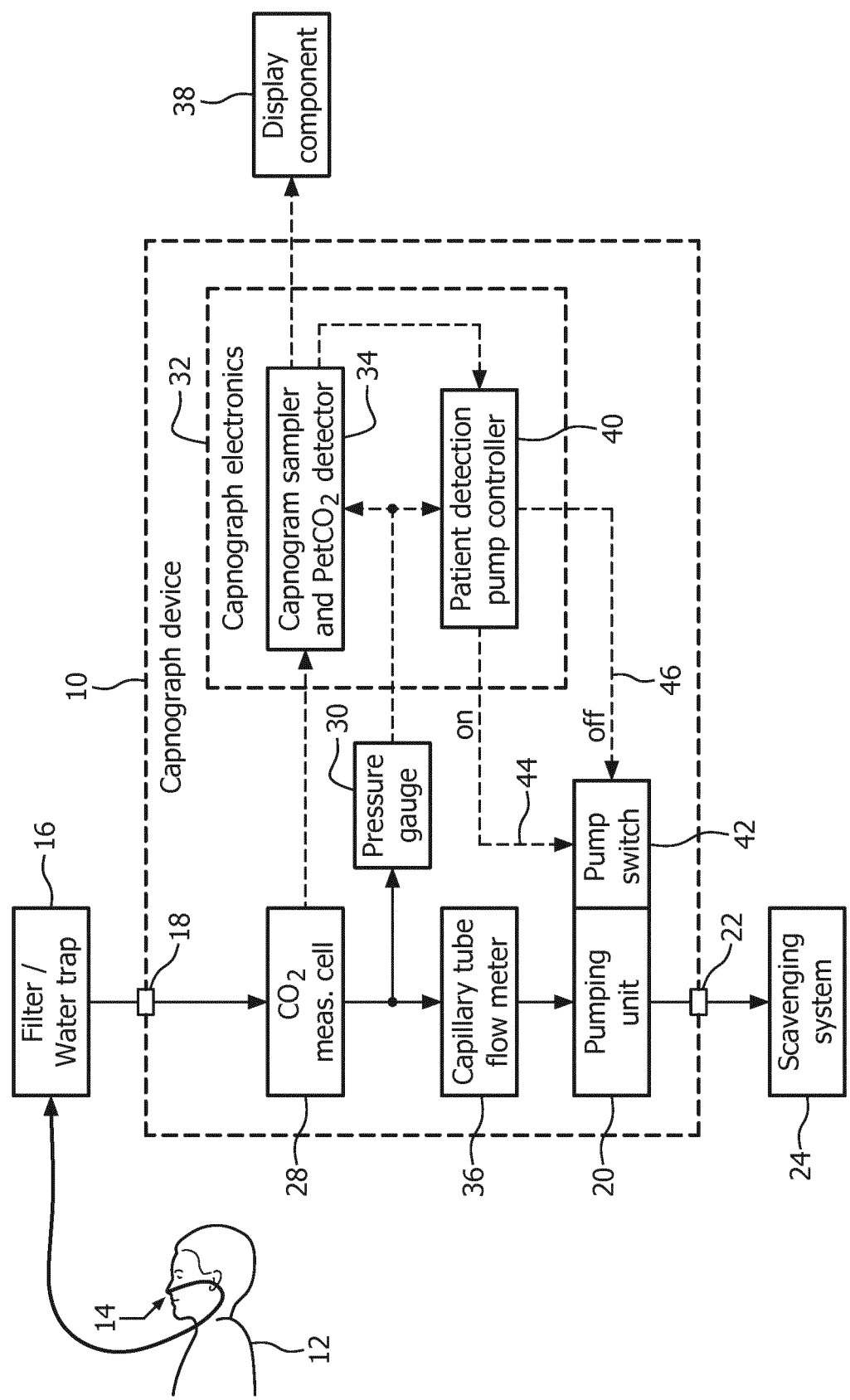
FIG. 1 diagrammatically illustrates a capnograph device.

With reference to FIG. 1, an illustrative capnograph device 10 is diagrammatically shown. In FIG. 1, air flow pathways are indicated by solid lines connecting components along the air flow path, while electrical or electronic signals are indicated by dotted arrows. As shown in FIG. 1, during operation the illustrative capnograph device 10 is connected with a patient 12 by a suitable patient accessory (or sampling accessory), such as an illustrative nasal cannula 14 in the illustrative example, or by an airway adaptor or so forth. The patient accessory 14 may optionally include one or more ancillary components, such as an illustrative air filter/water trap assembly 16 (that is, the complete patient accessory 14, 16 in the illustrative example includes the nasal cannula 14 and the connected filter/water trap assembly 16). Air is drawn from the patient accessory 14, 16 into the capnograph air inlet 18 by a pumping unit 20, and the air is discharged from an air outlet 22 of the capnograph 10 to atmosphere or, as in the illustrative embodiment, into a scavenging system 24 to remove an inhaled anesthetic or other inhaled medicinal agent.

The illustrative capnograph device 10 includes a carbon dioxide ($CO_2$) measurement component or cell 28, for example an infrared optical absorption cell, through which respired air is drawn from the patient accessory 14, 16 via the inlet 18 for analysis. A pressure gauge 30 measures the pressure (e.g., gauge pressure) of air in the air flow path through the capnograph device 10. Capnograph electronics 32 implement a capnography data processing component 34 that samples the $CO_2$ signal from the $CO_2$ measurement cell 28 to generate a capnogram (that is, a data stream of $CO_2$ level samples versus time, normalized in accordance with a chosen scale, e.g. as a partial pressure of $CO_2$ scaled using the pressure provided by the pressure gauge 30. The capnography data processing component 34 typically also computes the end-tidal $CO_2$ level, e.g. expressed as a partial pressure ($PetCO_2$), which is defined as the maximum $CO_2$ level observed over a breath cycle. Optionally, a capillary tube flow meter 36 or other flow meter provides further information for the $CO_2$ level data analysis (connection of the air flow signal from the flow meter 36 to the data processing component 34 is not shown in FIG. 1). Clinical data output by the capnograph 10, such as the capnogram and the $PetCO_2$ value for each breath, are displayed on a display component 38, stored in an electronic medical record (EMR) or the like, or otherwise utilized. The display component 38 may be a component of the capnograph or, as illustrated in FIG. 1, the display component 38 may be an external display component connected to the capnograph 10. For example, the external display component 38 may be a multi-function bedside patient monitor and/or a nurses' station patient monitor or so forth.

The pressure gauge 30 is a conventional component of a typical commercial capnograph device or other respiratory gas analyzer device, and is conventionally used to provide a pressure reading for air flow through the capnograph for use in assessing partial pressure values or other respiratory gas analysis functionality.

As recognized herein, the pressure gauge 30 is also suitably used to detect operational connection of the patient 12 to the inlet 18 of the capnograph device 10 so as to turn on the pump 20 only when a patient is in operational connection with the device 10. To this end, the capnograph electronics 32 are further programmed to implement a patient detection-based pump controller 40 that turns on the pump 20 in response to detecting operational connection of the patient 12 to the inlet 18 of the capnograph device 10 via the pressure gauge 30. In particular, a rapid change in this pressure is recognizes as indicating a reasonable likelihood that a patient has been operatively connected to the inlet 18.

In response to detection of a rapid change in pressure (greater than some chosen threshold), a pump switch 42 of the pumping unit 20 is activated (e.g. by sending an "on" signal 44 to the switch 42) to turn on the pump 20. As further disclosed herein, in some embodiments the patient detection-based pump controller 40 further performs a validation operation to validate that the detected pressure change is actually due to operational connection of a patient. This validation may be based on a detected rapid decrease in the pressure measured by the pressure gauge 30 upon the pump 20 being turned on. A rapid pressure decrease is indicative of the pump 20 drawing against a significant air flow resistance, such as is expected to be encountered when the air inlet 18 is operatively connected with the patient 12; by contrast, if the air flow path is "open" because no patient accessory 14, 16 is connected to the inlet 18, or alternatively the patient accessory 14, 16 is connected but no patient is connected with the patient accessory 14, 16. Another suitable validation criterion is observation of a pressure waveform as a function of time that cycles in accord with natural breathing or a known mechanical ventilation mode. As a secondary validation metric, when the $CO_2$ measurement cell 28 readout is stable (usually a few seconds after pump turn on, e.g. 4 sec in some illustrative examples herein) the operational patient connection can be directly validated by detecting whether a physically reasonable $CO_2$ reading is obtained.

If the validation is unsuccessful then the pump 20 is immediately turned off, e.g. by sending an "off" signal 46 to the pump switch 42. On the other hand, if the validation is successful then the pump 20 runs as per normal capnograph device operation until a pump turn off criterion is met (e.g. the pressure goes to zero, or the $CO_2$ level goes to zero, over some time interval), at which time the "off" signal 46 is sent to turn off the pump 20.

It will be appreciated that the described pumping unit 20 with on/off switch 42 that is turned on by a designated "on" signal 44 or off by a designated "off" signal 46 is merely an illustrative example, and that numerous other pump operation configurations can be employed. For example, the capnograph electronics may be configured to send a power signal to the pumping unit which powers the pump, in which case the patient detection-based pump controller 40 applies the pump power signal to turn the pump on (i.e. to operate the pump) and removes the pump power signal to turn the pump off. In such embodiments, the on/off switch 42 may be omitted.

It will be further appreciated that the capnograph electronics 32 may be variously implemented, such as by a suitably programmed electronic processor, e.g. a microprocessor or microcontroller of the capnograph 10. While a single electronics unit 32 is illustrated, it is alternatively contemplated to employ various combinations of electronics, for example the $CO_2$ data processing component 34 may be implemented by a first microprocessor or microcontroller while the patient detection-based pump controller 40 may be implemented by a separate second microprocessor or microcontroller. In such embodiments, the second microprocessor or microcontroller may optionally be built into the pump itself. It will be still further appreciated that the patient detection-based pump control functionality may be embodied by a non-transitory storage medium storing instructions that are readable and executable by the microprocessor, microcontroller, or other electronic processor to perform the patient detection-based pump control as disclosed herein. Such non-transitory storage media may, by way of non-limiting illustration, include a hard disk drive or other magnetic storage medium, a flash memory, read-only memory (ROM) or other electronic storage medium, an optical disk or other optical storage medium, various combinations thereof, or so forth.

Figure 2:
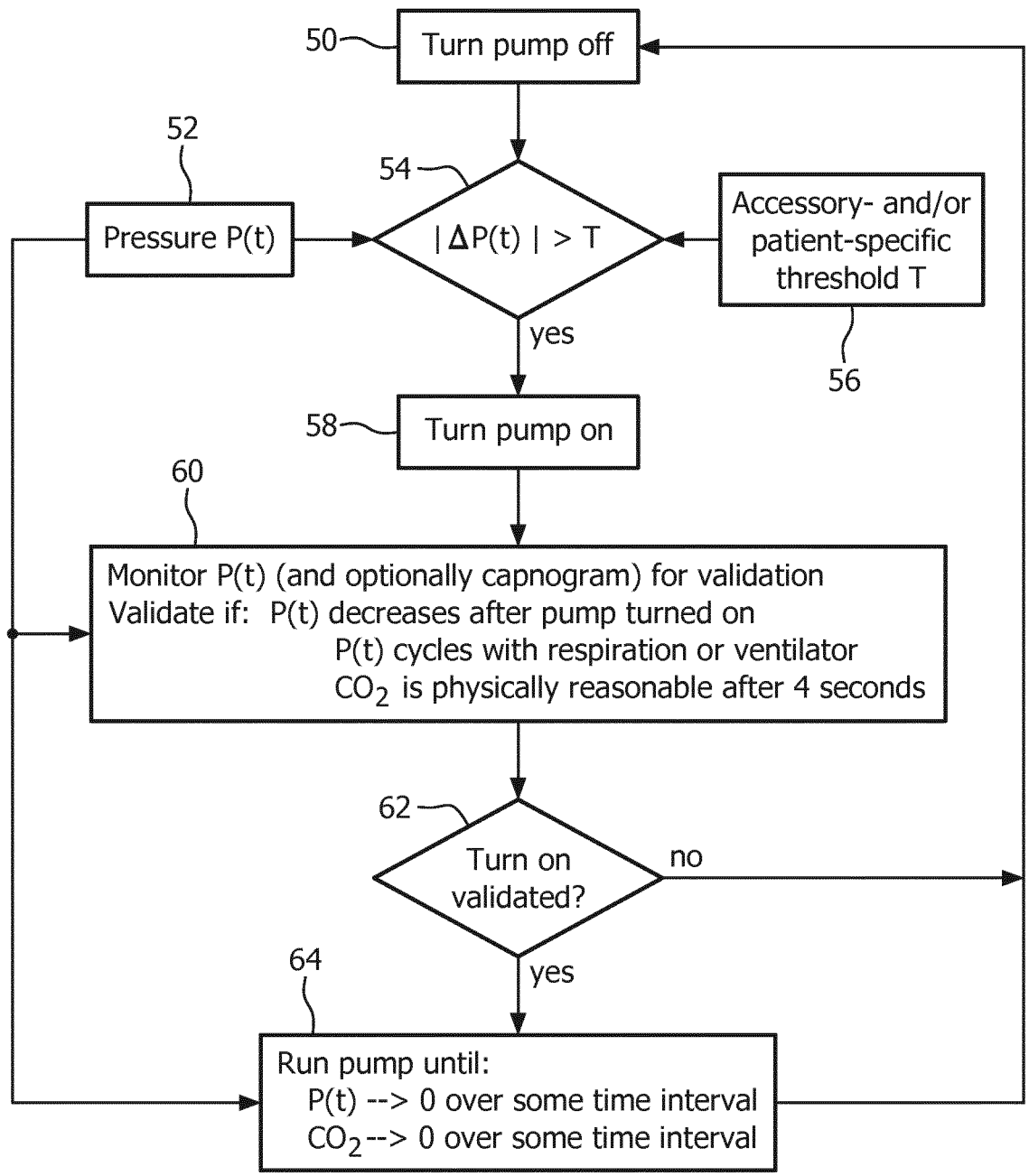
FIG. 2 diagrammatically illustrates a patient detection-based pump control process suitably performed by the patient detection-based pump controller of the capnograph device of FIG. 1.

With reference now to FIG. 2, an illustrative patient detection-based pump control process suitably performed by the patient detection-based pump controller 40 is described. The process starts with the pump 20 turned off in a starting state 50. The input for the patient detection includes the pressure 52 from the pressure gauge 50. The measured pressure as a function of time is denoted herein as P(t) where t denotes time. In an operation 54, the pressure 52 is monitored to detect a change in pressure, denoted herein as ΔP, that is greater than a pressure change threshold 56, denoted herein as T. That is, the operation 54 detects the patient operational connection condition $|\Delta P(t)| > T$ where $|\ldots|$ denotes absolute value (that is, $|\Delta P|$ is the magnitude of the abrupt pressure change. In this expression the pre-selected time interval over which the pressure change ΔP is measured may also be a parameter—since the expectation is that patient connection will produce an abrupt change in the measured pressure 52, this pre-selected time interval is preferably short, in some embodiments on the order of 1-2 seconds or shorter. In some embodiments, the pressure change threshold 56 may be a configurable parameter of the capnograph 10. For example, the threshold 56 may be smaller for an elderly or infant patient, or may be higher for a patient receiving strong mechanical ventilation. The length of the patient accessory 14, 16 or the presence/absence of flow impedance-adding intervening components such as the illustrative filter/trap 16 may also impact the optimal value for the threshold 56. It is also contemplated to configure the threshold 56 based on the criticality of achieving rapid capnograph measurement. For example, a capnograph device being used in a doctor's office may be preferably set with a high threshold (and thus is slower to turn on which extends pump operational life) as compared with a capnograph device used in a critical care unit where the threshold 56 is set to a low value (potentially reduced pump life is beneficially sacrificed here to ensure rapid $CO_2$ measurement for a critically ill patient).

It will also be appreciated that the operation 54 may employ a pump turn on criterion other than the illustrative criterion $|\Delta P(t)| > T$. For example, if it is expected that operational connection of a patient will produce only an increase in pressure (and not a decrease), then the pump turn on criterion may be $\Delta P(t) > T$. As a further example, rather than detecting an abrupt pressure change, the pump turn on criterion may be based on detecting a breathing waveform, for example observing periodicity over a time interval encompassing several breaths that has an expected respiratory periodicity. More generally, the pump turn on criterion is an observable feature of the pressure P(t) 52 measured by the pressure gauge 30 that is characteristic of operative connection of the capnograph device 10 (and more particularly the inlet 18) to a patient who is being mechanically ventilated or breathing without assistance from a mechanical ventilator.

When the patient connection condition $|\Delta P(t)| > T$ is met, the pump 20 is turned on in an operation 58. Thereafter, a validation operation 60 is optionally performed to verify that a patient has indeed been operatively connected. The validation operation 60 advantageously leverages additional information that becomes available upon the pump 20 being turned on, or leverages other information. For example, in the case of connection to a patient who breathing on his or her own, it is expected that the pressure 52 will decrease rapidly when the pump 20 is turned on because the pump draws against a relatively high flow impedance produced by the patient accessory 14, 16 connected with the patient 12. Thus, this validation criterion may be expressed as $-\Delta P|_{pump\ on} < T_{val}$ where the negative sign indicates a pressure decrease and $T_{val}$ is a validation threshold which again may be a configurable parameter of the capnograph device 10, as the optimal threshold may depend on various factors such as the type of patient accessory (e.g. nasal cannula size, or airway adapter, et cetera), the pressure in the main airway, or so forth.

In the case of a patient on a mechanical ventilator, it is possible that the expected pressure decrease may be "masked" by a rising main airway pressure due to the mechanical ventilation forcing air into the lungs during the inspiration phase. Another suitable validation criterion is a metric of whether the pressure P(t) cycles over time with the expected patient breathing (under force of the patient's diaphragm or assisted or driven by mechanical ventilation). A metric of the form $|P_{max} - P_{min}|_{T_{breath}} > T_{val2}$ may be used, where $T_{breath}$ is chosen to be long enough to encompass at least one breath cycle (typically around least 3-6 seconds) and the difference $P_{max} - P_{min}$ is the observed pressure variation over this time interval. Additionally or alternatively, a time-based criterion may be used, e.g. the time interval between consecutive pressure maxima or between consecutive pressure minima is expected to correspond to a single breath.

As another example of a validation criterion, the patient connection may be validated if the maximum pressure $P_{max}$ over a time interval is greater than some threshold. This validation criterion may be particularly useful in the case of a mechanically ventilated patient with an airway adapter patient accessory, such that the full maximum pressure applied by the ventilator is observed by the capnograph device 10.

In some embodiments, the validation operation 60 may additionally or alternatively use the actual $CO_2$ reading (or other measured respired gas component) output by the $CO_2$ measurement cell 28 (or other gas measurement component) for validation of the pump start up. Typically, it takes a few seconds (e.g. 4 seconds in some devices) for the $CO_2$ reading to stabilize. If a physically reasonable $CO_2$ value is measured by the measurement cell 28 after this stabilization interval, then patient connection is validated. A physically reasonable $CO_2$ value may, for example, be quantified as the end-tidal $CO_2$ level (conventionally denoted as $etCO_2$ and conventionally defined as the maximum $CO_2$ level observed during a breathing cycle) exceeding some minimum threshold $T_{etCO2}$; that is, the validation criterion is $etCO_2 > T_{etCO2}$. A disadvantage of this approach is that there is the stabilization delay, but an advantage is that this validation directly operates on the $CO_2$ reading—that is, the pump turn on is validated if there is in fact an operation connection of the capnograph device 10 to a patient 12. This criterion will also ensure that the pump does not turn on if the $CO_2$ measurement component 28 is malfunctioning so as to output a false-low (e.g. zero) $CO_2$ level, even if the capnograph 10 is properly connected with the patient, thus ensuring the capnograph 10 does not run unnecessarily while generating bad $CO_2$ level data.

In an operation 62, it is determined from the output of the validation operation 60 whether or not the pump turn on is validated, that is, whether or not a patient is verified to be operationally connected to the capnograph 10. If only one patient connection validation criterion is employed then this determination is straightforward. If more than one patient connection validation criterion is employed then the outputs of the two or more criteria may be variously combined, e.g. validating patient connection if any one of the validation criteria is met; or alternatively, validating only if all of the patient validation criteria are met. In some embodiments, a more reliable criterion may "override" a less reliable criterion—for example, if the $CO_2$ reading is reasonable (which is a direct indication that a patient is operatively connected) then the operation 62 may optionally conclude a patient is connected even if the pressure decrease upon pump turn on does not meet the threshold $T_{val}$ and/or the pressure waveform is not consistent with a typical respiratory cycle.

If the operation 62 determines that patient connection is not validated, then flow returns to operation 50 which turns off the pump 20 after which the pump controller 40 returns to the monitoring operation 54.

On the other hand, if the operation 62 determines that patient connection is validated, then process control passes to an operation 64 which runs the pump 20 (i.e. keeps the pump 20 on) until a turn off criterion is met. For example, a suitable turn-off criterion is the pressure decreasing to a value sufficiently close to zero, that is, $P(t) \to 0$ over a certain time interval sufficient to avoid pump shutoff due to spurious pressure drops (e.g. an interval of a few seconds to a few tens of seconds to avoid turning off the pump during the inspiration phase of the breathing cycle). Another suitable turn-off criterion is the carbon dioxide measured by the $CO_2$ measurement cell 28 decreasing to a value sufficiently close to zero, that is, $CO_2(t) \to 0$ over a certain time interval sufficient to avoid pump shutoff due to spurious $CO_2$ reading drops (e.g. an interval of a few seconds to a few tens of seconds to avoid turning off the pump during the inspiration phase of the breathing cycle). When the turn-off criterion is met, flow returns to operation 50 which turns off the pump 20 after which the pump controller 40 returns to the monitoring operation 54.

Although not illustrated, it is contemplated to employ the disclosed patient detection-based pump controller 40 in combination with a patient accessory that has a mechanical or optical connection switch. In one approach for such a combination, the pump does not turn on unless both the patient detection as described with reference to FIG. 2 is met and the appropriate mechanical or optical switch input is received from the patient accessory. On the other hand, it will be appreciated that an advantage of the disclosed capnograph device 10 is that it can be used in conjunction with patient accessories that have no such mechanical or optical switch included either with the patient accessory or with the inlet of the capnograph device.

As previously mentioned the pump control algorithm of FIG. 2 (or similar patient detection-based pump control algorithms) may optionally employ turn on, turn off, and/or patient validation parameters (e.g. thresholds) that are configurable parameters of the capnograph device. In a convenient approach for this configuration, the user may input the patient type (e.g. neonate, mechanically ventilated, et cetera) and/or the patient accessory type (cannula, airway adapter) and the pump controller 40 then reads the appropriate thresholds for that type of patient/connection from a look-up table.

The illustrative embodiment comprises a capnograph device 10. More generally, it will be appreciated that the disclosed patient detection-based pump control may be advantageously employed in conjunction with any type of respiratory gas analyzer device that employs a pump to draw respired gas into a gas measurement component for sampling. The gas measurement component may be a $CO_2$ measurement component 28 (as illustrated), or may be a gas measurement component for measuring a partial pressure or other metric of oxygen, various volatile organic compounds, or other respired gas components.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A respiratory gas analyzer device for use with a patient who is being mechanically ventilated or breathing without assistance from a mechanical ventilator, comprising:
   a housing of the respiratory gas analyzer device, the housing comprising an inlet configured to fluidly couple the respiratory gas analyzer device to a patient accessory, wherein the patient accessory delivers gas to the patient independent of the respiratory gas analyzer device;
   a gas measurement component, the gas measurement component being fluidly coupled to the inlet and configured to measure at least one respired gas component;
   a pump, the pump being configured to draw respired gas from the patient accessory and through the inlet to the gas measurement component;
   a pressure gauge connected to measure pressure in an airflow pathway including the gas measurement component and the pump; and
   an electronic pump controller programmed to:
      start the pump in response to pressure measured by the pressure gauge satisfying a pump turn on criterion;
      thereafter determine that validation for the start of the pump failed based on (i) a pressure criterion which is a function of pressure measured by the pressure gauge, indicating an open airflow circuit and (ii) a respired gas component criterion which is a function of measured respired gas component output by the gas measurement component; and
      turn off the pump after validation fails.

2. The respiratory gas analyzer device of claim 1 wherein the electronic pump controller is programmed to start the pump in response to a change in pressure measured by the pressure gauge of magnitude greater than a pump turn on threshold.

3. The respiratory gas analyzer device of claim 2 wherein the change in pressure is measured over a pre-selected time interval of 2 seconds or less.

4. The respiratory gas analyzer device of claim 1 wherein the pump turn on criterion is $|\Delta P(t)| > T$, where $P(t)$ is the pressure as a function of time measured by the pressure gauge, $|\Delta P(t)|$ is a pressure change magnitude over a pre-selected time interval, and T is a pump turn on threshold.

5. The respiratory gas analyzer device of claim 2 wherein the pump turn on threshold is a configurable parameter of the respiratory gas analyzer device whose value is configured based on one or more of patient type and patient accessory type.

6. The respiratory gas analyzer device of claim 1 wherein the pump turn on criterion is an observable feature of the pressure measured by the pressure gauge that is characteristic of operative connection of the respiratory gas analyzer device to a patient who is being mechanically ventilated or breathing without assistance from a mechanical ventilator.

7. The respiratory gas analyzer device of claim 1 wherein the validation is further based on a pressure criterion that includes one or more of (i) a pressure decrease after pump startup and (ii) cycling of pressure after pump startup.

8. The respiratory gas analyzer device of claim 1 wherein:
- the gas measurement component includes a carbon dioxide measurement component and the measured respired gas component includes a carbon dioxide measurement; and
- the respired gas component criterion includes the measured end-tidal carbon dioxide ($etCO_2$) measured by the carbon dioxide measurement component exceeding a threshold ($T_{etCO2}$).

9. The respiratory gas analyzer device of claim 1 wherein the respiratory gas analyzer device comprises a capnograph device in which the gas measurement component comprises a carbon dioxide ($CO_2$) measurement component.

10. The respiratory gas analyzer device of claim 1, wherein the pump is configured to discharge the respired gas to atmosphere or into a scavenging system.

* * * * *